(12) United States Patent
Castro

(10) Patent No.: US 9,456,907 B1
(45) Date of Patent: Oct. 4, 2016

(54) EXTENDABLE SPINAL IMPLANT

(71) Applicant: IGIP, LLC, Louisville, KY (US)

(72) Inventor: Frank Castro, Louisville, KY (US)

(73) Assignee: IGIP, LLC, Louisville, KY (US)

( * ) Notice: Subject to any disclaimer, the term of this patent is extended or adjusted under 35 U.S.C. 154(b) by 231 days.

(21) Appl. No.: 14/187,654

(22) Filed: Feb. 24, 2014

Related U.S. Application Data

(63) Continuation-in-part of application No. 12/804,867, filed on Jul. 30, 2010, now Pat. No. 8,673,006, and a continuation-in-part of application No. 12/583,865, filed on Aug. 27, 2009, now Pat. No. 8,246,683, and a continuation-in-part of application No. 12/583,864, filed on Aug. 27, 2009, now Pat. No. 8,361,149, and a continuation-in-part of application No. 12/290,069, filed on Oct. 27, 2008, now Pat. No. 8,226,718, and a continuation-in-part of application No. 12/221,779, filed on Aug. 6, 2008, now Pat. No. 8,002,832, and a continuation of application No. 11/089,103, filed on Mar. 24, 2005, now Pat. No. 7,435,261.

(51) Int. Cl.
*A61F 2/44* (2006.01)

(52) U.S. Cl.
CPC ........ *A61F 2/447* (2013.01); *A61F 2002/4475* (2013.01)

(58) Field of Classification Search
CPC .................. A61F 2/4455; A61F 2/447; A61F 2002/4475; A61F 2002/448; A61F 2002/449; A61F 2/44; A61F 2/4425; A61F 2/4465; A61F 2/446
See application file for complete search history.

(56) References Cited

U.S. PATENT DOCUMENTS

| | | | |
|---|---|---|---|
| 5,147,402 A * | 9/1992 | Bohler et al. | 623/16.11 |
| 5,192,327 A * | 3/1993 | Brantigan | 623/17.11 |
| 5,290,312 A * | 3/1994 | Kojimoto | A61F 2/44 606/247 |
| 5,405,391 A * | 4/1995 | Hednerson et al. | 623/17.15 |
| 5,425,772 A | 6/1995 | Brantigan | |
| 5,458,638 A | 10/1995 | Kuslich et al. | |
| 5,558,674 A | 9/1996 | Heggeness et al. | |
| 5,609,635 A | 3/1997 | Michelson | |
| 5,766,252 A | 6/1998 | Henry et al. | |
| 5,888,228 A | 3/1999 | Knothe et al. | |
| 5,968,098 A | 10/1999 | Winslow | |
| 5,980,522 A | 11/1999 | Koros et al. | |
| 6,066,175 A | 5/2000 | Henderson et al. | |
| 6,080,193 A | 6/2000 | Hochshuler et al. | |
| 6,090,143 A | 7/2000 | Meriwether et al. | |
| 6,117,174 A | 9/2000 | Nolan | |
| 6,159,211 A * | 12/2000 | Boriani et al. | 606/279 |
| 6,159,245 A | 12/2000 | Meriwether et al. | |
| 6,200,348 B1 * | 3/2001 | Biedermann et al. | 623/17.11 |
| 6,231,610 B1 | 5/2001 | Geisler | |

(Continued)

FOREIGN PATENT DOCUMENTS

GB 2364643 2/2002

OTHER PUBLICATIONS

Barack, R. L. Revision Total Hip Arthoplasty: The Femoral Component. J. Am Acad Orthop Surg 1995; 3(2); 79-85. USA.

(Continued)

*Primary Examiner* — Lynnsy Summitt
(74) *Attorney, Agent, or Firm* — Kenneth F. Pearce

(57) ABSTRACT

The present invention is an extendable surgical implant that can be inserted into a surgically created cavity.

20 Claims, 4 Drawing Sheets

(56) References Cited

U.S. PATENT DOCUMENTS

| | | | |
|---|---|---|---|
| 6,287,343 B1 | 9/2001 | Kuslich et al. | |
| 6,302,914 B1 | 10/2001 | Michelson | |
| 6,395,030 B1 | 5/2002 | Songer et al. | |
| 6,395,035 B2 | 5/2002 | Bresina et al. | |
| 6,409,766 B1 | 6/2002 | Brett | |
| 6,419,705 B1* | 7/2002 | Erickson | 623/17.16 |
| 6,432,107 B1 | 8/2002 | Ferree | |
| 6,491,724 B1 | 12/2002 | Ferree | |
| 6,537,320 B1 | 3/2003 | Michelson | |
| 6,562,074 B2 | 5/2003 | Gerbec et al. | |
| 6,569,201 B2 | 5/2003 | Moumene et al. | |
| 6,576,016 B1 | 6/2003 | Hochshuler et al. | |
| 6,582,432 B1 | 6/2003 | Michelson | |
| 6,613,091 B1 | 9/2003 | Zdeblick et al. | |
| 6,641,614 B1 | 11/2003 | Wagner et al. | |
| 6,648,917 B2 | 11/2003 | Gerbec et al. | |
| 6,660,038 B2 | 12/2003 | Boyer et al. | |
| 6,712,825 B2 | 3/2004 | Aebi et al. | |
| 6,712,852 B1 | 3/2004 | Chung et al. | |
| 6,746,484 B1 | 6/2004 | Liu et al. | |
| 6,761,738 B1 | 7/2004 | Boyd | |
| 6,767,367 B1 | 7/2004 | Michelson | |
| 6,776,798 B2 | 8/2004 | Camino et al. | |
| 6,805,714 B2 | 10/2004 | Sutcliffe | |
| 6,808,538 B2 | 10/2004 | Paponneau | |
| 6,852,129 B2 | 2/2005 | Gerbec et al. | |
| 6,863,673 B2 | 3/2005 | Gerbec et al. | |
| 6,926,737 B2 | 8/2005 | Jackson et al. | |
| 6,929,662 B1 | 8/2005 | Messerli et al. | |
| 6,942,697 B2 | 9/2005 | Lange et al. | |
| 6,997,953 B2 | 2/2006 | Chung et al. | |
| D524,942 S | 7/2006 | Felix | |
| 7,166,110 B2 | 1/2007 | Yundt | |
| 7,182,782 B2 | 2/2007 | Kirschman | |
| 7,232,463 B2 | 6/2007 | Falahee | |
| 7,435,261 B1* | 10/2008 | Castro | 623/17.11 |
| 7,621,953 B2 | 11/2009 | Braddock, Jr. et al. | |
| 7,641,701 B2 | 1/2010 | Kirschman | |
| 7,803,191 B2* | 9/2010 | Biedermann | A61F 2/44 606/246 |
| 8,585,761 B2* | 11/2013 | Theofilos | A61F 2/44 623/17.11 |
| 8,673,011 B2* | 3/2014 | Theofilos | A61F 2/447 623/17.11 |
| 9,023,107 B2* | 5/2015 | Muhanna | A61F 2/442 623/17.15 |
| 9,308,098 B2* | 4/2016 | Boehm | A61F 2/44 |
| 2002/0099443 A1 | 7/2002 | Messerli et al. | |
| 2003/0125739 A1 | 7/2003 | Bagga et al. | |
| 2003/0199980 A1 | 10/2003 | Siedler | |
| 2004/0064184 A1 | 4/2004 | Chung et al. | |
| 2004/0073314 A1 | 4/2004 | White et al. | |
| 2004/0126407 A1 | 7/2004 | Falahee | |
| 2004/0153155 A1 | 8/2004 | Chung et al. | |
| 2004/0153160 A1* | 8/2004 | Carrasco | A61F 2/4611 623/17.15 |
| 2004/0199254 A1 | 10/2004 | Louis et al. | |
| 2004/0204714 A1 | 10/2004 | Liu et al. | |
| 2004/0225360 A1 | 11/2004 | Malone | |
| 2005/0071006 A1 | 3/2005 | Kirschman | |
| 2005/0071008 A1 | 3/2005 | Kirschman | |
| 2005/0149192 A1 | 7/2005 | Zucherman | |
| 2005/0159813 A1 | 7/2005 | Molz IV, et al. | |
| 2006/0058879 A1 | 3/2006 | Metz-stavenhagen | |
| 2006/0287725 A1 | 12/2006 | Miller | |
| 2007/0016295 A1 | 1/2007 | Boyd | |
| 2007/0123987 A1 | 5/2007 | Bernstein | |
| 2007/0129805 A1 | 6/2007 | Braddock, Jr. et al. | |
| 2007/0250167 A1 | 10/2007 | Bray et al. | |
| 2007/0255409 A1 | 11/2007 | Dickson et al. | |
| 2007/0255413 A1 | 11/2007 | Edie et al. | |
| 2008/0015694 A1 | 1/2008 | Tribus | |
| 2008/0021476 A1 | 1/2008 | Kirschman | |
| 2008/0132901 A1 | 6/2008 | Recoules-arche et al. | |
| 2008/0275506 A1 | 11/2008 | Baynham et al. | |
| 2008/0281424 A1* | 11/2008 | Parry | A61F 2/4455 623/17.16 |
| 2009/0036985 A1 | 2/2009 | Whiting | |
| 2009/0234364 A1 | 9/2009 | Crook | |
| 2010/0004752 A1 | 1/2010 | White et al. | |
| 2010/0179656 A1* | 7/2010 | Theofilos | 623/17.11 |
| 2011/0087328 A1* | 4/2011 | Dickson | A61F 2/44 623/17.11 |
| 2012/0016476 A1* | 1/2012 | Wilfong | A61F 2/44 623/17.11 |
| 2013/0158669 A1* | 6/2013 | Sungarian et al. | 623/17.16 |
| 2013/0197648 A1* | 8/2013 | Boehm | A61F 2/44 623/17.16 |
| 2014/0277501 A1* | 9/2014 | Northcutt et al. | 623/17.16 |

OTHER PUBLICATIONS

Castro, F. P., Jr. Stingers, Cervical Cord Neurapraxia, and Stenois. Clin Sport Med 2003; 22 483-492. USA.

Majd M.E., Vadhva, M., Holt R. T. Anterior Cervical Reconstruction Using Titanium Cages With Anterior Plating. Spine 1999I 24 (15): 1604-1610. USA.

Park J. B., Cho Y.S., Riew, K.D. Development of Adjacent-Level Ossification in Patient wian an Anterior Cervical Plate. J. Bone Surg. 1005; 87-A; 558-563. USA.

* cited by examiner

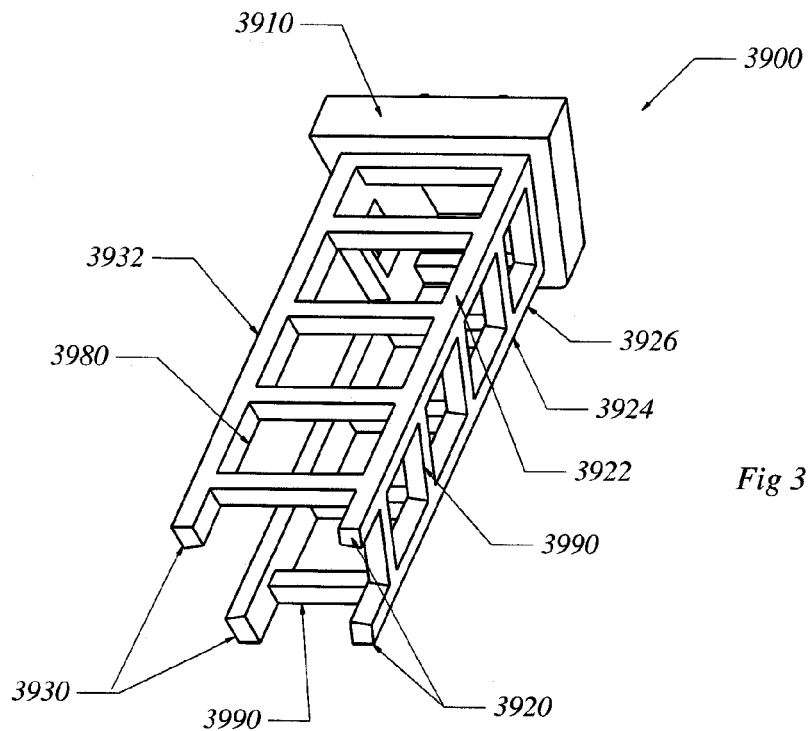
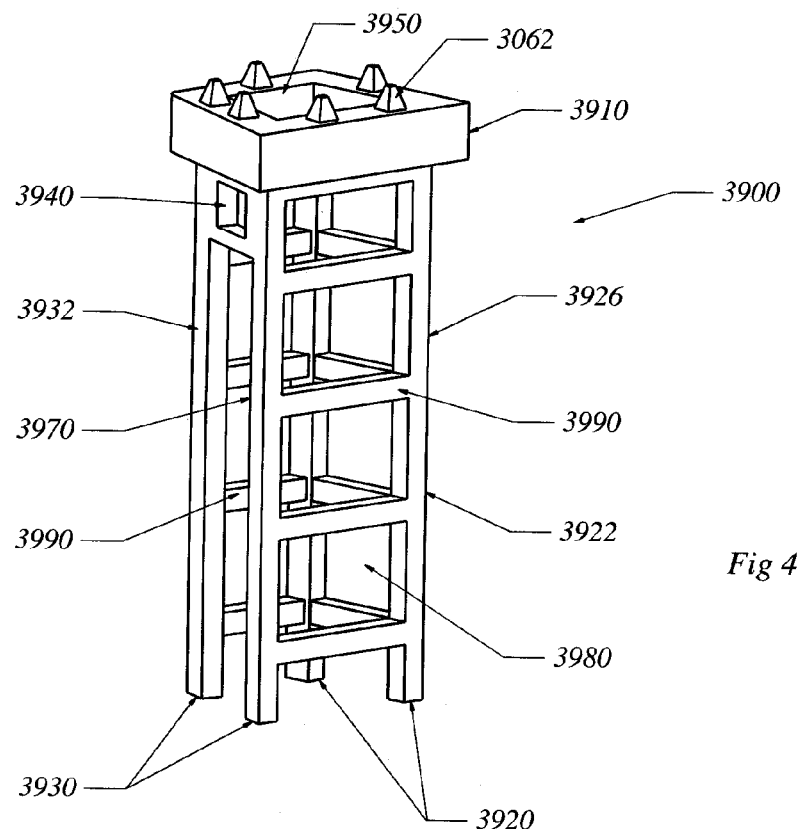

EXTENDABLE SPINAL IMPLANT

This Application is a Continuation-in-Part of pending Application for Letters patent Ser. No. 12/804,867 entitled—Spinal Implant—filed on Jul. 30, 2010 that is a Continuation-In-Part of Applications for Letters Patent Ser. No. 12/583,865 entitled Spinal Implant—filed on Aug. 27, 2009, now U.S. Pat. No. 8,246,683 issued on Aug. 21, 2012, and Application for Letters Patent Ser. No. 12/583,864 entitled—Wedge-Like Spinal Implant—filed on Aug. 27, 2009, now U.S. Pat. No. 8,361,149 issued Jan. 29, 2013, wherein the Applications for Letters patent Ser. No. 12/583,864 and Ser. No. 12/583,865 are Continuations-In-Part of Application for Letters Patent, Ser. No. 12/290,069, entitled—Spinal Implant and Method of Using Spinal Implant—filed on Oct. 27, 2008, now U.S. Pat. No. 8,226,718 issued Jul. 24, 2012, that is a Continuation-In-Part of Application for Letters Patent, Ser. No. 12/221,779 entitled—Spinal Implant and Method of Using Spinal Implant—filed on Aug. 6, 2008, now U.S. Pat. No. 8,002,832 issued Aug. 23, 2011, that is a Continuation of Application for Letters Patent, Ser. No. 11/089,103 entitled—Spinal Implant and Method of Using Spinal Implant—filed on Mar. 24, 2005, now U.S. Pat. No. 7,435,261 issued on Oct. 14, 2008.

BACKGROUND OF THE INVENTION

A. Field of the Invention

Among other things, the present invention is related to an extendable surgical implant that can be inserted into a cavity that has been created by removing spinal tissue. Post operative and prior to complete arthrodesis, the current invention inhibits extrusion of the cage against the spinal cord.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

Some of the references believed by Applicant to be potentially relevant to the current state-of-the-art are set forth below. Additional references potentially material to the current state-of-the-art are identified in Applicant's accompanying Statement under 37 C.F.R. §1.56.

U.S. Pat. No. 6,926,737-Jackson, et al. enables a spinal fusion apparatus and method. The '737 Patent discloses, "The fusion enhancing apparatus 1 includes a pair of bone receiving cages or implants 10 and 11 that are joined to a connecting plate 12 that joins a pair of end caps 15 and 16 by a pair of set screws 13 and 14 respectively." Among other things, it does not appear that the Jackson invention practices the use of a spinal implant utilizing a cage and an extendable member having slides for engaging the channel of the cage.

U.S. Pat. No. 6,409,766-Brett enables a collapsible and expandable interbody fusion device. The '766 Patent reads, "A fusion cage 10 of the present invention includes an upper body 12 connected to a lower body 14 by side articulated supports 16, 18. The fusion cage 10 expands and contracts between a fully open or expanded position (FIGS. 1 and 2), through a midway, partially collapsed position (FIGS. 3 and 4), to a fully closed or collapsed position (FIGS. 5 and 6)." Among other things, it does not appear that the Brett invention practices the use of a spinal implant utilizing a cage and an extendable member having slides for engaging the channel of the cage.

US Published Patent Application 20040073314-White, et al. teaches vertebral body and disc space devices. The '314 Application discloses, "[0055] In FIGS. 1-2, a vertebral replacement device 10 includes a connecting member 12, an upper member 30, and a lower member 40. Device 10 is illustrated as having a tubular form that extends along a longitudinal axis 11 and defines a chamber extending therethrough along axis 11. Bone growth can occur through this chamber for fusion between the vertebral bodies supported at each end of device 10." Among other things, it does not appear that the White invention practices the use of a spinal implant utilizing a cage and an extendable member having slides for engaging the channel of the cage.

US Published Patent Application 20060287725-Miller teaches a lateral expandable interbody fusion cage. The '725 Application discloses, "The laterally expandable interbody fusion cage of the present invention comprises an outer cage 12 and an inner cage 14 that can be inserted sideways into the outer cage 12. The inner cage 14 has a notch 16 for an expander to grip on the front of the inner cage 14. The inner cage 14 can be filled with graft material prior to insertion." Among other things, it does not appear that the Miller invention practices the use of a spinal implant utilizing a cage and an extendable member having slides for engaging the channel of the cage.

US Published Patent Application 20100004752-White, et al. teaches vertebral body and disc space replacement devices. The '752 Application discloses, "Referring now to FIGS. 22-23, there is shown another embodiment vertebral replacement device 500. Vertebral replacement device 500 includes one or more upper or lower end or disc replacement members 600, 601 and one or more connecting or vertebral body members 510 engaged to disc replacement members 600, 601. Vertebral replacement device 500 has application in corpectomy procedures in which one or more vertebrae are removed. Applications in disc space replacement and interbody fusion procedures are also contemplated. In the illustrated embodiment, vertebral replacement device 500 includes three members stacked one upon the other. Other embodiments contemplate two member stacks, or stacks comprising four or more members." Among other things, it does not appear that the White invention practices the use of a spinal implant utilizing a cage and an extendable member having slides for engaging the channel of the cage.

US Published Patent Application 20090036985-Whiting teaches vertebral fusion parts, devices and methods. The '985 Application discloses, "FIG. 5 shows a perspective view of the components of an intervertebral fusion device or assembly 170 including end plate 140, end cap 100 and cage or mesh element 180. Cage 180 is generally cylindrical having an oval cross-section and is made of a titanium mesh. Cage 180 can also be made of other biocompatible materials, such as stainless steel or non-metallic materials. Cage 180 has a first edge 182 and a second edge 184 at opposed ends of the cage. Edges 182, 184 are defined by mesh parts and also recess parts formed by incomplete apertures of the mesh. As illustrated in FIG. 5, cage 180, end cap 100 and end plate 140 are all in registration centred on the central longitudinal axis of cage 180 passing through the centre of the oval. To assemble the intervertebral fusion device, end cap 100 is presented to the open end of cage 180 and push fitted into the open end of cage 170 in the direction of arrow 172. As tongues 110, 112 and 114 are flexible, they deform sufficiently to allow end cap 100 to be introduced into the free end of cage 170 until flange 106 engages with the outer edge 182 of cage 170 to limit further motion of end cap 100 into cage 180. The chamfered edges of skirts 120, 122, 124 also help to facilitate engagement of the end cap and cage and the skirts also help to centre and securely seat the end cap in the end of cage 170. Tongues 110, 112 and 114 are also resilient members and urge their barbs into engagement with the inner surface of cage 180 so as to retain end cap 100 in cage 180. The outer side of end cap 100 can then be presented to the underside of end plate 140 by engaging the outer part of annular body 102 into aperture 148 of end plate 140." Among other things, it does not appear that the Whiting invention practices the use of a spinal implant utilizing a cage including a border with apertures for receiving fasteners and an extendable member having slides for engaging the channel of the cage.

US Published Patent Application 20070123987-Bernstein teaches a curvilinear cervical interbody device. The '987 Application discloses, "As seen in FIGS. 1 and 2, the spacer assembly 100 includes an upper end piece 110 and a lower end piece 112. End piece 110 comprises an exterior surface 110a in first end plate 110b, integrally formed flange 142 for attaching the assembly to a vertebral body, and stepped or ratcheting connectors 130a, 130b, 131. End piece 112 comprises an exterior surface 112a on second end plate 112b, integrally formed flange 144, and stepped or ratcheting connectors 132a, 132b, 133. End piece 112 is shown with an optional stabilizing piece 140 connecting ratcheting connectors 132a, 132b and 133, for instance by going around the perimeter of the end piece 112, providing additional structural integrity to the end piece. Thus, when the two end pieces are assembled, the tendency of the internal ratcheting connectors 130a, 130b, 131 to push out the external connectors 132a, 132b, 133 is minimized by the presence of the connecting piece 140." Among other things, it does not appear that the Bernstein invention practices the use of a spinal implant utilizing a cage including a border with apertures for receiving fasteners and an extendable member having slides for engaging the channel of the cage where the fasteners secure the slides.

US Published Patent Application 20020099443-Messerli, et al. teaches an end member for a bone fusion implant. The '443 Application discloses, "The present invention relates to an end member for use with a bone fusion implant for fusing portions of bone. The end member has a first portion, a second portion sized to be inserted into the bore of the implant, and a shoulder between the first and second portions. When the second portion is inserted into the bore, the shoulder rests on an edge of the implant. The top surface of the first portion conforms in size and shape with the bone and has a channel or multiple channels for receiving a surgical instrument. When multiple channels are present, all the channels can run in the same direction, (e.g. the channels run in the anterolateral direction), or the channels can run in different directions, (e.g. a first channel runs in the anterior-posterior direction and a second channel runs in the lateral direction)." Among other things, it does not appear that the Messerli invention practices the use of a spinal implant utilizing a cage and an extendable member having slides for engaging the channel of the cage.

US Published Patent Application 20030199980-Siedler teaches a vertebral column implant. The '980 Application discloses, "[0039] As illustrated in FIG. 1, the preferred embodiment of the vertebral column implant according to the present invention is composed of five implant elements, i.e., a first outer implant element 1, a central base element 2, an implant element 3 located between the first outer implant element 1 and the central base element 2, a second outer implant element 4 and an implant element 5 located between the central base element 2 and the second outer implant element 4. These five implant elements can be securely connected to each other and, in the connected state form the vertebral column implant according to the present invention. The two outer implant elements 1 and 4 each have an anchoring side 6 and 7 facing an adjacent vertebra, wherein the anchoring sides 6 and 7 are provided with recesses with side surfaces which include an angle of about 90 degrees with each other so as to form peaks 8, as illustrated in FIGS. 2 and 6. These peaks 8 form a toothing which ensures that a displacement of the vertebral column implant is prevented toward all sides. On their sides facing away from the anchoring side 6 and 7, the two outer implant elements 1 and 4 are each provided tongues 10, 11 which extend parallel to the axis along the wall of a central bore 9. These tongues 10, 11 have holding edges 12, 13 which extend transversely at the outer ends of the tongues; in the connected state, the holding edges 12, 13 engage behind or grasp a support edge in the area of the bore of the adjacent implant element. Consequently, these tongues 10, 11 form a plug-type connection through which the implant elements 1 through 5 can be connected to each other to form astable vertebral column implant." Among other things, it does not appear that the Siedler invention practices the use of a spinal implant utilizing a cage including a border with apertures for receiving fasteners and an extendable member having slides for engaging the channel of the cage where the fasteners secure the slides.

SUMMARY OF THE INVENTION

Unlike traditional spinal implants, the present invention provides an extendable biocompatible spinal implant that assists the surgical team in not impinging the spinal cord with the extendable spinal implant. Post operative and prior to complete arthrodesis, the wedge-like preferred embodiments of the spinal implant inhibit extrusion of the cage against the spinal cord. It has been discovered that the spinal implant's biocompatible cage and the extendable member combination is particularly useful for assisting in the restoration of normal anatomical height and angulation of an abnormal vertebral body. It has also been discovered that the biocompatible cage and the extendable extension combination is particularly useful for assisting in the restoration of normal anatomical height and angulation of an abnormal vertebral body.

An aspect of the present invention is to provide a biocompatible spinal implant.

Still another aspect of the present invention is to provide a spinal implant utilizing a cage and extendable member.

It is still another aspect of the present invention to provide a spinal implant having select embodiments that can be implanted through the patient's frontal or rearward side.

Yet still another aspect of the present invention is to provide a spinal implant utilizing lateral brakes.

Still another aspect of the present invention is to provide a cage with a border utilizing a catch, slit and plurality of apertures.

Yet another aspect of the present invention is to provide an extendable extension with a margin with slides extending from the margin for a channel of the cage.

It is still another aspect of the present invention to provide an extendable extension capable of extending the length of the spinal implant.

Still another aspect of the present invention is to utilize a tool connectable with the extendable member and the cage for adjusting the length of the spinal implant.

Yet another aspect of the present invention is to provide a biocompatible spinal implant with a plurality of openings to increase the probability of the osteogenic materials procuring a blood supply.

A preferred embodiment of the current invention can be described as an extendable spinal implant comprising: a cage comprising four load-bearing sides creating a trapezoidal channel traversing a length of the cage, wherein each load-bearing side includes openings therein for allowing passage of osteogenic substances into a surgically created cavity; the cage further comprising: a) an inward load-bearing side of lessor dimensions than the dimensions of an outward load-bearing side; b) a first lateral side comprising a border contacting the inward load-bearing side and the outward load-bearing side; the border surrounding one of the openings and comprising: i) a catch proximate a first lengthwise end of the cage; ii) a slit in a second lengthwise end of the cage opposite said catch; and iii) a plurality of apertures for receiving one or more fasteners; and c) a first plurality of spikes extending longitudinally from the first lengthwise end; and an extendable member comprising: a) a margin comprising a to trapezoidal orifice and a plurality of points extending from the margin in directions analogous to or parallel with the spikes; b) a first slide extending from the margin engaging an inner side of the inward load-bearing side; c) a second slide extending from the margin engaging an inner side of the outward load-bearing side, wherein widths of the slides are adequate for engagement by one or more fasteners; d) a first edge comprising a notch proximate the margin; and e) a second edge, opposite the first edge, connected with the first and second slides, wherein the slides and the second edge further comprise ties.

Another preferred embodiment of the current invention can be described as a spinal implant for implantation into a surgically created cavity; the spinal implant comprising a cage and an extendable extension: said cage comprising: a) four load-bearing sides including one or more openings surrounding a channel, wherein an inward load-bearing side is of lessor periphery than a periphery of an outward load-bearing side, and wherein the openings expose osteogenic substances within the channel; b) a first lateral side comprising a border; the border comprising: i) a catch proximate a first lengthwise end of the cage; and ii) a slit in the border opposite the first lengthwise end; and iii) a plurality of apertures for receiving one or more fasteners; c) a second lateral side opposite the first lateral side having a periphery similar to the first lateral side's periphery; and d) at least one spike extending longitudinally from a first lengthwise end of the cage; and the extendable extension comprising: a) a margin comprising one or more points extending from the margin in directions analogous to or parallel with at least one spike; b) first and second opposed slides extending from said margin engaging inner sides of the channel, wherein widths of the slides are adequate for engagement by one or more fasteners; and c) a first edge connected with said first and second slides; the first edge comprising a notch proximate the margin.

Still another preferred embodiment of the current invention can be described as a spinal implant for implantation into a surgically created cavity; the spinal implant comprising a cage and an extendable extension: the cage comprising: a) a plurality of sides including one or more openings surrounding a channel; b) a first side comprising a border; the border comprising: i) a catch connectable with an expansion tool distinct from the cage; and ii) a slit in a second lengthwise end of the border opposite the catch; and iii) a plurality of apertures for receiving one or more fasteners; and c) a plurality of spikes extending longitudinally from a first lengthwise end of the cage; and the extendable extension comprising: a) first and said second opposed slides engaging inner sides of the channel, wherein the slides extend from a margin comprising one or more points extending in directions analogous to or parallel with the plurality of spikes; and b) a notch proximate the margin and connectable with the expansion tool such that the expansion tool adjusts a distance the extendable extension extends from the cage.

Yet another preferred embodiment of the current invention can be described as a spinal implant for implantation into a surgically created cavity; the spinal implant comprising a cage and an extendable extension: the cage comprising: a) a plurality of sides including one or more openings surrounding a channel, wherein the openings expose osteogenic substances within the channel; and b) a first side comprising a border; the border comprising: i) a catch connectable with an expansion tool; and ii) a slit in a second lengthwise end of the border opposite the catch; and iii) a plurality of apertures for receiving one or more fasteners; and the extendable extension comprising: a) first and second opposed slides engaging inner sides of the channel, wherein the slides extend from a margin; and b) a notch proximate the margin and connectable with the expansion tool such that the expansion tool adjusts a distance the extendable extension extends from the cage.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 3 is a first lateral perspective of a preferred embodiment of a biocompatible extendable member or extension of the extendable spinal implant.

FIG. 4 is a second lateral perspective of a preferred embodiment of a biocompatible extendable member or extension of the extendable spinal implant.

DESCRIPTION OF THE PREFERRED EMBODIMENTS

Figure 1:
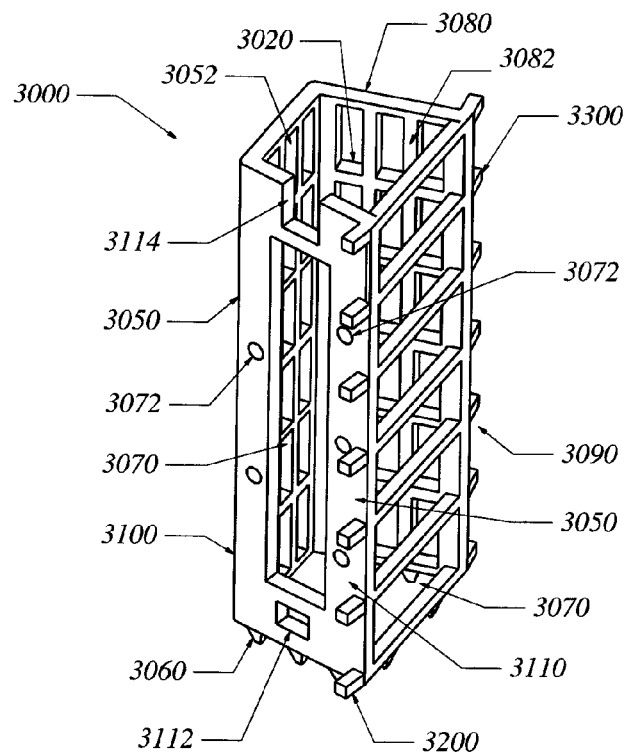
FIG. 1 is a lateral perspective of a preferred embodiment of a biocompatible cage of the extendable spinal implant.

Although the disclosure hereof is detailed to enable those skilled in the art to practice the invention, the embodiments published herein merely exemplify the present invention.

In the most general sense, the present invention is an extendable spinal implant that can be inserted into a cavity of a spinal column. Surgical removal of mammalian spinal tissue in one or more spinal regions creates the cavity or cavities that will receive the implant or implants. It has been discovered that many embodiments of the current implant can be useful for spine surgeries and can assist in stabilizing injured, deformed and or degenerative spines. Preferred embodiments of the current invention can be employed with thoracic or lumbar spinal procedures. Still other preferred embodiments of the present invention are particularly suited for corpectomy or partial corpectomy procedures.

After insertion of the implant into the cavity, the spinal implant's biocompatible cage and the extendable extension combinations assist in stabilizing the spinal column against rotational movement and the combinations also resist the compression forces associated with gravity on the spinal column. It has been discovered that the spinal implant's biocompatible cage and the extendable extension combination is particularly useful for assisting in the restoration of normal anatomical height and angulation of an abnormal vertebral body. Select preferred embodiments of the present invention can be implanted through the patient's anterior or ventral side.

Preferred embodiments of the current spinal implant's cage are generally trapezoidal in shape and are manufactured of titanium alloys, stainless steel, resorbable polymers, non-resorbable polymers or any other composition acceptable in the art. Preferred embodiments of the current spinal implant's extendable extension, when expanded, increase the length of the spinal implant to a size compatible with the surgical cavity into which the spinal implant is implanted. Preferred embodiments of the current extendable extension are manufactured of titanium alloys, stainless steel, resorbable polymers, non-resorbable polymers or any other composition acceptable in the art.

Openings of the current spinal implant allow passage of bone graft, osteogenic and/or arthrodesis accelerating substances into predetermined portions of the surgically created cavity. Prior to extension of the spinal implant, preferred embodiments of the spinal implant and extendable extension have lengths that range from about 15 millimeters to about 60 millimeters. When the spinal implant's extension is extended, about 15 millimeters or more of length is added to the extendable spinal implant from the spinal implant's unextended length. Width dimensions of preferred embodiments of the cage range from about 20 millimeters to about 45 millimeters, and depth dimensions range from about 20 millimeters to about 30 millimeters. In select preferred embodiments, margins of the extendable extension reciprocate in first and second planes with the cage of the spinal implant. Slides can extend away from the margin of for distances of from about 3 millimeters to about 15 millimeters. Some preferred embodiments of the present spinal implant are provided with one or more spikes at opposite ends of the spinal implant for engaging bone. Among other things, preferred embodiments of the spinal implant's cage and extendable extension are provided with catches and notches for fitting with an expansion tool for adjusting the length of the extendable spinal implant.

Meeting a long felt but unfilled need in the spinal surgical arts, the unique structures of the present combinations allow the surgical team to, among other things, enhance the length of the spinal column from about two millimeters to about twenty millimeters more than the length of the biocompatible cage, when the patient's medical condition requires. Contact between the surgical cavity wall and the wedge-like spinal implant can also inhibit the implant from contacting the spinal cord. It appears that having the spinal implant's openings in proximity with the surgical cavity's walls increases the probability of the osteogenic materials procuring a blood supply. And it is believed that increasing the blood supply to the osteogenic materials held by the spinal implant enhances local areas of arthrodesis between the vertebra and the bone graft. Select preferred embodiments of the present spinal implant are provided with lateral brakes to impede the implant from contacting the spinal column.

Figure 2:
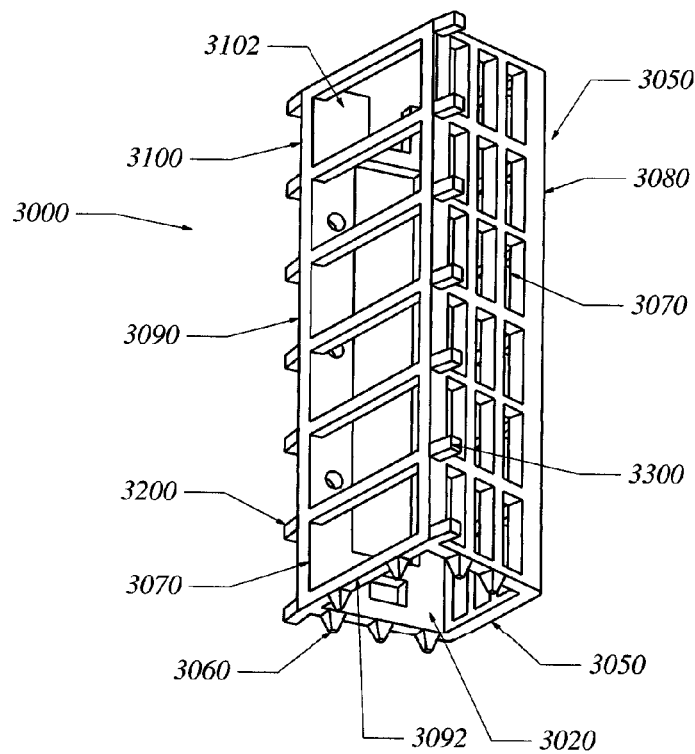
FIG. 2 is a frontal perspective of a preferred embodiment of a biocompatible cage of the extendable spinal implant.

FIG. 1 is a lateral perspective of biocompatible cage (3000) of extendable spinal implant (3600). FIG. 2 is a frontal perspective of cage (3000) of spinal implant (3600).

As shown in the preferred embodiment portrayed in FIGS. 1 and 2, spinal facing side or inward side (3050) of cage (3000) is lessor dimensions than outward side (3090). Lateral side (3080) of cage (3000) connects with inward side (3050) and outward side (3090) of cage (3000). Opposite lateral (3080) is lateral-load bearing side (3100) connected with inward side (3050) and outward side (3090). For selected preferred embodiments of cage (3000), interconnected inward load-bearing side (3050), outward load-bearing side (3090) and lateral load-bearing sides (3080, 3100) form the cage (3000) of extendable spinal implant (3600). Within the scope of the current invention, select preferred embodiments of cage (3000) are provided with one or more lateral brakes (3200, 3300) capable of impeding advancement of the spinal implant toward the spinal cord potentially exposed by the surgically created cavity. In select preferred embodiments of spinal implant (3600), a lengthwise end of cage (3000) can be provided with spikes (3060) extending longitudinally from a lengthwise end of cage (3000). Spikes (3060) are capable of engaging bone or vertebra and further stabilizing spinal implant (3600) after implantation into the surgically created cavity.

As shown in FIGS. 1 and 2, inner side (3052) of inward load-bearing side (3050), inner side (3082) of lateral load-bearing side (3080), inner side (3092) of outward load-bearing side (3090) and inner side (3102) of lateral side (3100) of cage (3000) create generally trapezoidal channel (3020) traversing the length of cage (3000). Although select preferred embodiments of cage (3000) utilize a channel (3020) that is generally trapezoidal, within the scope of the current invention, other cages (3000) can include a channel (3020) that is not generally trapezoidal. In vivo, channel (3020) of cage (3000) can be supplied with osteogenic materials. Inward side (3050), lateral side (3080), outward side (3090) and lateral side (3100) of cage (3000) are provided with one or more openings (3070) exposing osteogenic substances to the surgically created cavity.

With a view toward FIG. 1, lateral side (3100) of cage (3000) is provided with border (3110) contacting inward side (3050), lateral side (3080), outward side (3090) and lateral side (3100) of cage (3000). Border (3110) surrounds opening (3070) and is provided with one or more apertures (3072) for receiving fasteners (not shown in FIG. 1). As shown in FIG. 1, opening (3070) of border (3110) is generally rectangular in shape; however, other sizes of opening (3072) are within the ambit of the present invention. Catch (3112) is proximate a lengthwise end of cage (3000) and connectable with an expansion tool distinct (not shown) from spinal implant (3600). Slit (3114) is provided in border (3110) opposite an end of border (3110) proximate catch (3112).

FIG. 3 is a first lateral perspective of biocompatible extendable member or extension (3900) of extendable spinal implant (3600). FIG. 4 is a second lateral perspective of extendable member or extension (3900) of spinal implant (3600).

As shown in FIGS. 3 and 4, a preferred embodiment of extension (3900) of spinal implant (3600) includes margin (3910) and slide (3920) and slide (3930) extending longitudinally from margin (3910). Slide (3930) is provided with edge (3932) including notch (3940) proximate margin (3910). Notch (3940) is connectable with an expansion tool distinct (not shown) from spinal implant (3600). As shown, ties (3990) interconnect slide (3920) and slide (3930) and legs (3922, 3924) of edge (3926) of extension (3900). After extension of extendable member (3900) of spinal implant (3600), osteogenic substances can be loaded into compartment (3970) created by slides (3920, 3930) and edges (3932, 3926) of extension. Openings (3980) created by ties (3990) allow passage of osteogenic substances into the surgically creative cavity. However, select preferred embodiments of extension (3900) are functional without ties (3990).

As shown in FIG. 4, margin (3910) is provided with trapezoidal orifice (3950). Points (3062) extend from margin (3910) in longitudinal directions analogous to or parallel with spikes (3060) of cage (3000) of spinal implant (3600). Points (3062) are capable of engaging bone or vertebra and further stabilizing spinal implant (3600) after implantation into the surgically created cavity.

Figure 5:
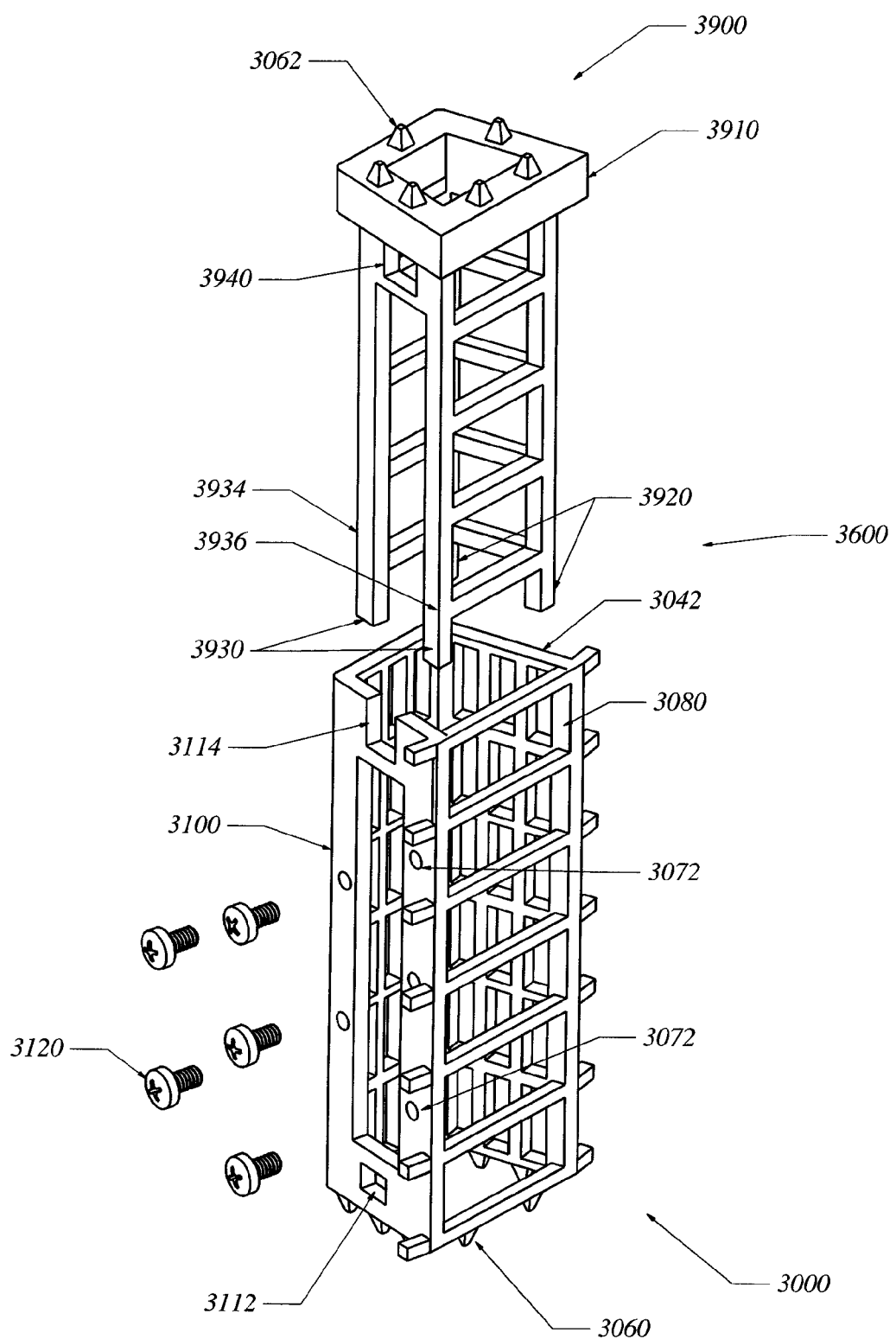
FIG. 5 is an exploded perspective of a preferred embodiment of an extendable spinal implant.

FIG. 5 is an exploded perspective of spinal implant (3600). As shown, for operative preferred embodiments of spinal implant (3600), notch (3940) of extension (3900) is aligned with slit (3114) of cage (3000). Slide (3920) fits against inner side of lateral side (3080) and slide (3930) fits against inner side of lateral side (3100). In a preferred embodiment shown in FIG. 5, slide (3930) is provided with legs (3934, 3936) of adequate width for secure engagement by one or more fasteners (3120) fitted through one or more apertures (3072) of border (3110) of cage (3000). From an unextended position of spinal implant (3600), an extension tool can connect notch (3940) of extendable member (3900) and catch (3112) of cage to cause extendable member (3900) to extend outward from cage (3000) to the a length determined by the surgical team implanting spinal implant (3600). In select preferred embodiments of spinal implant (3600), margin (3910) of extension (3900) and lengthwise end (3042) of cage (3000) have reciprocating planes with respect to width and depth.

Figure 6:
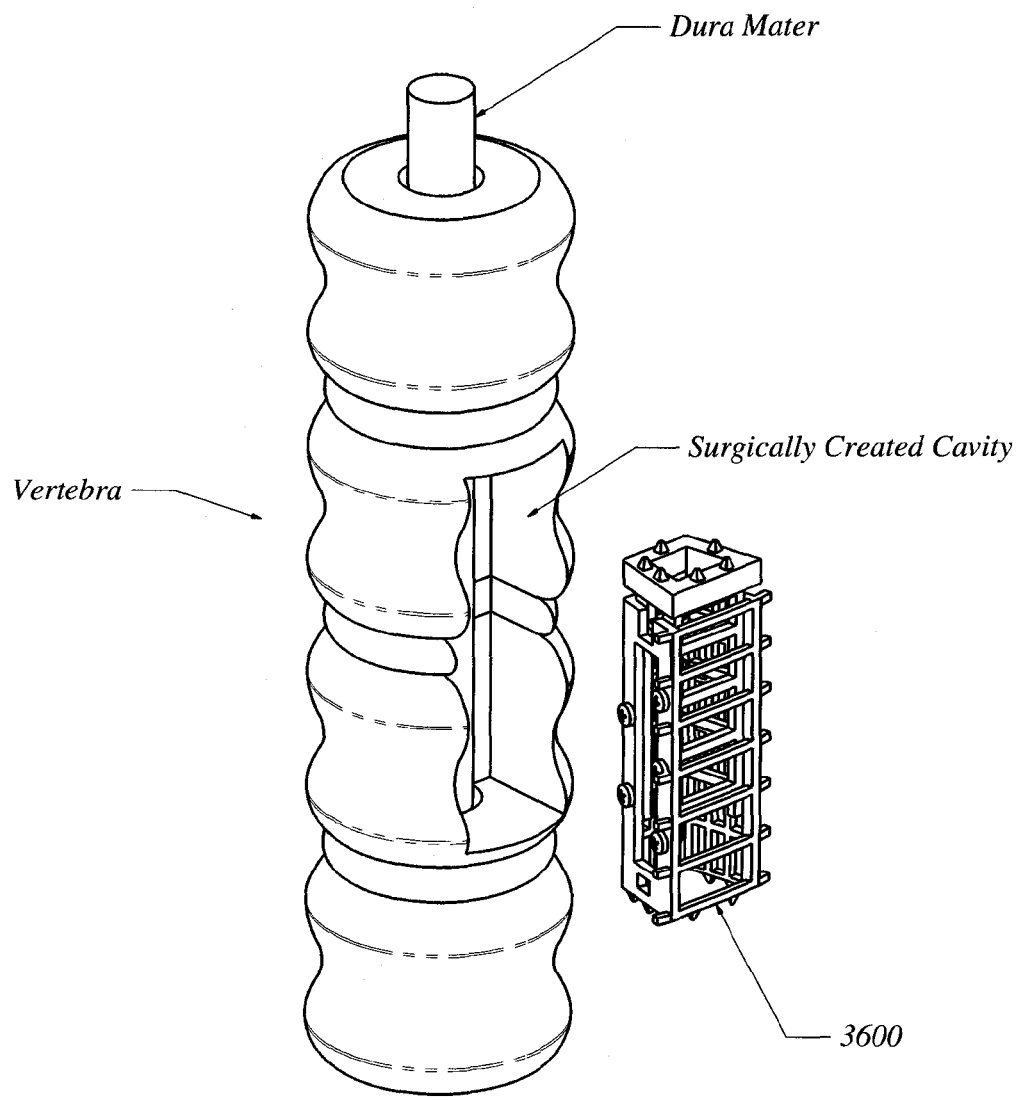
FIG. 6 is a depiction of a preferred embodiment of an extendable spinal implant that has been inserted into a surgically created cavity created in a spine.

FIG. 6 is a depiction of a preferred embodiment of extendable spinal implant (3600) that has been inserted into a surgically created cavity created in a spine.

Having disclosed the invention as required by Title 35 of the United States Code, Applicant now prays respectfully that Letters Patent be granted for his invention in accordance with the scope of the claims appended hereto.

What is claimed is:

1. An extendable spinal implant comprising:
   a) a cage comprising four load-bearing sides creating a trapezoidal channel traversing a length of said cage, wherein an outward load bearing side is wider than an inward load bearing side and each of said four load-bearing sides includes openings therein for allowing passage of osteogenic substances into a surgically created cavity,
   wherein one of said four load bearing sides comprises a border lateral said trapezoidal channel and contacting said inward load-bearing side and said outward load-bearing side; said border surrounding one of said openings and comprising:
      i) a catch proximate a first lengthwise end of said cage;
      ii) a slit in a second lengthwise end of said cage opposite said catch and having a common longitudinal axis with said catch and said one of said openings; and
      iii) at least one aperture positioned on each lateral side of said border, on either side of said one of said openings and adapted for receiving one or more fasteners;
   b) a first plurality of spikes extending longitudinally from said first lengthwise end; and
   c) an extendable member comprising:
      i) a margin comprising a trapezoidal orifice and a plurality of points extending from said margin in directions analogous to or parallel with said spikes;
      ii) a first slide extending from said margin engaging an inner side of said inward load-bearing side;
      iii) a second slide extending from said margin engaging an inner side of said outward load-bearing side, wherein widths of said slides are adequate for engagement by said one or more fasteners;
      iv) a first edge comprising a notch lateral said trapezoidal channel and proximate said margin; and
      v) a second edge, opposite said first edge, connected with said first and second slides, wherein said slides and said second edge further comprise ties.

2. The spinal implant of claim 1, wherein said border comprises more than one aperture positioned on at least one lateral side of said border.

3. The spinal implant of claim 2, wherein said cage and said margin comprise reciprocating sizes in a first plane and a second plane of said spinal implant.

4. A spinal implant for implantation into a surgically created cavity; said spinal implant comprising a cage and an extendable extension:
   said cage comprising:
      a) four load-bearing sides including one or more openings surrounding a channel, wherein each of said load-bearing sides comprises at least one opening and several of said load-bearing sides comprise more than one opening, and wherein an inward load-bearing side is of lessor periphery than a periphery of an outward load-bearing side;
      b) one of said load-bearing sides comprising a border lateral said channel; said border surrounding one of said openings and comprising:
         i) a catch proximate a first lengthwise end of said cage;
         ii) a slit in said border opposite said catch and having a common longitudinal axis with said catch and said one of said openings surrounded by said border; and
         iii) at least one aperture positioned on each lateral side of said border, on either side of said one of said openings and adapted for receiving one or more fasteners; and
      c) at least one spike extending longitudinally from a first lengthwise end of said cage; and
   said extendable extension comprising:
      a) a margin comprising one or more points extending from said margin in directions analogous to or parallel with said at least one spike;
      b) first and second opposed slides extending from said margin engaging inner sides of said channel, wherein widths of said slides are adequate for engagement by said one or more fasteners; and
      c) a first edge connected with said first and second slides; said first edge comprising a notch lateral said channel and proximate said margin.

5. The spinal implant of claim 4, wherein said border comprises more than one aperture positioned on at least one lateral side of said border.

6. The spinal implant of claim 5, wherein a span of said channel is generally trapezoidal.

7. The spinal implant of claim 6, wherein said cage and said margin comprise reciprocating sizes in a first plane and a second plane of said spinal implant.

8. The spinal implant of claim 7 comprising ties for a second edge opposite said first edge and said first and second slides.

9. A spinal implant for implantation into a surgically created cavity; said spinal implant comprising a cage and an extendable extension:
   said cage comprising:
   a) a plurality of sides surrounding a channel, wherein each of said sides comprises at least one opening and several of said sides comprise more than one opening;
   b) one of said sides further comprising a border lateral said channel surrounding one of said openings; said border comprising:
      i) a catch connectable with an expansion tool distinct from said cage;
      ii) a slit in said border opposite said catch and having a common longitudinal axis with said catch and said one of said openings surrounded by said border; and
      iii) at least one aperture positioned on each lateral side of said border, on either side of said one of said openings and adapted for receiving one or more fasteners; and
   c) a plurality of spikes extending longitudinally from a first lengthwise end of said cage; and
   said extendable extension comprising:
   a) first and said second opposed slides engaging inner sides of said channel, wherein said slides extend from a margin comprising one or more points extending in directions analogous to or parallel with said plurality of spikes; and
   b) a notch lateral said channel and proximate said margin; said notch connectable with said expansion tool.

10. The spinal implant of claim 9, wherein more than one side of said extendable extension comprise ties.

11. The spinal implant of claim 10, wherein a span of said channel is generally trapezoidal.

12. The spinal implant of claim 11, wherein said openings expose osteogenic substances within said channel.

13. The spinal implant of claim 12, wherein said cage and said margin comprise reciprocating sizes in a first plane and a second plane of said spinal implant.

14. The spinal implant of claim 13, wherein said border comprises more than one aperture positioned on at least one lateral side of said border.

15. A spinal implant for implantation into a surgically created cavity; said spinal implant comprising a cage and an extendable extension:
   said cage comprising:
   a) a plurality of sides surrounding a channel, wherein each of said sides comprises at least one opening and several of said sides comprise more than one opening;
   b) one of said sides comprising a border lateral said channel; said border comprising:
      i) a catch connectable with an expansion tool;
      ii) a slit in a second lengthwise end of said border opposite said catch;
      iii) one of said openings spanning an approximate length of said border and having a common longitudinal axis with said catch and said slit; and
      iv) at least one aperture positioned on each lateral side of said one of said openings; said apertures adapted for receiving one or more fasteners; and
   said extendable extension comprising:
   a) first and second opposed slides engaging inner sides of said channel, wherein said slides extend from a margin; and
   b) a notch lateral said channel and proximate said margin; said notch connectable with said expansion tool.

16. The spinal implant of claim 15, wherein more than one side of said extendable extension comprise ties.

17. The spinal implant of claim 16 comprising:
   a) at least one spike extending longitudinally from a first lengthwise end of said cage; and
   b) at least one point extending from said margin in a direction analogous to or parallel with said at least one spike.

18. The spinal implant of claim 17, wherein a span of said channel is generally trapezoidal.

19. The spinal implant of claim 18, wherein said cage and said margin comprise reciprocating sizes in a first plane and a second plane of said spinal implant.

20. The spinal implant of claim 19, wherein said border comprises more than one aperture positioned on at least one lateral side of said border.

* * * * *